US009517302B2

United States Patent
Krogh

(10) Patent No.: US 9,517,302 B2
(45) Date of Patent: Dec. 13, 2016

(54) METHOD AND SYSTEM FOR ALERTING AS TO POTENTIAL FOR BOLUS CONDITION

(75) Inventor: Ross G. Krogh, Long Grove, IL (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 1122 days.

(21) Appl. No.: 13/487,723

(22) Filed: Jun. 4, 2012

(65) Prior Publication Data

US 2012/0310204 A1 Dec. 6, 2012

Related U.S. Application Data

(60) Provisional application No. 61/492,655, filed on Jun. 2, 2011.

(51) Int. Cl.
*A61M 5/168* (2006.01)

(52) U.S. Cl.
CPC ..... *A61M 5/16827* (2013.01); *A61M 5/16831* (2013.01)

(58) Field of Classification Search
CPC .............. A61M 5/168; A61M 5/16827; A61M 5/16831; A61M 5/172
See application file for complete search history.

(56) References Cited

U.S. PATENT DOCUMENTS

| 2005/0277911 | A1 | 12/2005 | Stewart et al. |
| 2007/0156089 | A1 | 7/2007 | Yu |
| 2008/0103445 | A1* | 5/2008 | Blaine ............... A61M 5/365 604/122 |
| 2010/0121170 | A1 | 5/2010 | Rule |
| 2011/0111794 | A1 | 5/2011 | Bochenko et al. |
| 2013/0218080 | A1* | 8/2013 | Peterfreund .......... A61M 5/142 604/151 |

FOREIGN PATENT DOCUMENTS

| EP | 1870121 | 12/2007 |
| WO | WO 96/25963 | 8/1996 |
| WO | WO 2010/043054 | 4/2010 |

OTHER PUBLICATIONS

International Search Report and Written Opinion for corresponding international application No. PCT/US2012/040475, mailing date Aug. 8, 2012.

* cited by examiner

*Primary Examiner* — Kami A Bosworth
(74) *Attorney, Agent, or Firm* — Marshall, Gerstein & Borun LLP

(57) ABSTRACT

A method of alerting a user to a potential unintended bolus delivery includes delivering fluid to a patient along a first fluid flow path. The method also includes transmitting a signal prior to initiation of a change in fluid delivery to the patient along a second fluid flow path connected to the first fluid flow path upstream of the patient, and detecting the signal. The method further includes actuating an alarm to alert the user to a potential unintended bolus delivery if the signal is detected. A system for carrying out the method is also provided.

22 Claims, 5 Drawing Sheets

METHOD AND SYSTEM FOR ALERTING AS TO POTENTIAL FOR BOLUS CONDITION

BACKGROUND

This patent is directed to a method and a system for alerting a user, such as a nurse or other healthcare professional, to a potential for a bolus condition, and, in particular, to a method and system for alerting a user to a potentially unintended bolus condition during concomitant fluid delivery to a patient.

Therapy, or treatment, for a medical condition may be characterized in a number of different ways. For example, therapy may be discussed in terms of the agent used to affect a change in the patient's condition, such as a drug or radiation. As another example, therapy may be discussed in terms of the mode or route of administration.

Infusion therapy—the intravenous delivery (i.e., delivery into a vein) of therapy, for example—is well known in the art. In its simplest form, infusion therapy may be carried out using a container or bag connected to a patient via a drip chamber, an administration set and a catheter. In such a system and according to such a method, fluid passes from the bag to the patient under the influence of gravity. In a more complex system, a pump or a cuff may be used to control the flow of the fluid to the patient.

For a number of reasons, healthcare providers prefer to share a common intravenous (IV) injection site when providing infusions of multiple fluids or drugs to a patient. Chief among the reasons for sharing a common site is the minimization of trauma to the patient. By using a common site, multiple needle sticks are avoided, with a reduced risk of infection and bruising as a consequence. Another important reason for using common IV injection sites is to minimize opportunity for patient movement to result in inadvertent separation of the infusion connection. Therefore, the providers (e.g., nurses) may set up a manifold or Y-site connection to facilitate sharing of the common injection site.

However, the same sharing of the injection site that prevents trauma and minimizes inadvertent separation may set up the conditions under which an unintended bolus of a drug may be delivered to the patient. For example, consider a situation where the site is already being used by a first fluid delivery device (such as a first pump) to deliver a fluid at a first delivery rate to the patient along a line having a Y-site connection. When a second fluid delivery device is connected to the patient using the Y-site connection and then actuated to deliver fluid at a second delivery rate through the Y-site connection, the flow rate of fluid downstream of the Y-site connection is accelerated to a rate equal to the sum of the first and second delivery rates. As the fluid path prior to initiation of the second infusion contains only the first infusate, this acceleration of the delivery of this fluid may have the effect of delivering a bolus of the fluid from the first delivery device to the patient until the second fluid also reaches the injection site, and yet the provider may not appreciate that this bolus is being delivered and may not intend for the bolus to be administered. With certain medications, the delivery of a bolus may have a significant adverse effect on the patient, and thus should be avoided if at all possible.

As set forth in greater detail below, the present disclosure sets forth an improved assembly embodying advantageous alternatives to the conventional devices and methods discussed above. In particular, the present disclosure addresses the significant unmet need in the area of systems and methods for alerting a healthcare provider to the potential for an unintended delivery of a bolus to patient.

SUMMARY

According to an aspect of the present disclosure, a system for alerting a user to a potential unintended bolus delivery includes a first fluid delivery system in fluid communication with a patient along a first fluid flow path, the first fluid delivery system having a receiver. The system also includes a second fluid delivery system in fluid communication with the patient along a second fluid flow path connected to the first fluid flow path between the first fluid delivery system and the patient, the second fluid delivery system having a transmitter in communication with the receiver and configured to provide a signal prior to initiation of the second fluid delivery system to change fluid delivery to the patient from the second fluid delivery system. The system further includes a controller coupled to the receiver, the controller programmed to determine if the signal has been received by the receiver and to alert the user to a potential unintended bolus delivery if the signal has been received by the receiver.

According to another aspect of the present disclosure, a method of alerting a user to a potential unintended bolus delivery includes delivering fluid to a patient along a first fluid flow path. The method also includes transmitting a signal prior to initiation of a change in fluid delivery to the patient along a second fluid flow path connected to the first fluid flow path upstream of the patient, and detecting the signal. The method further includes actuating an alarm to alert the user to a potential unintended bolus delivery if the signal is detected.

According to a further aspect of the present disclosure, a method of managing a first fluid delivery system having a first fluid flow path and a second fluid delivery system having a second fluid flow path connected to the first fluid flow path so as to avoid a potential unintended bolus delivery is provided. The method includes transmitting a signal prior to initiation of a change in fluid delivery to the patient along the second fluid flow path, detecting the signal, and actuating an alarm to alert the user to a potential unintended bolus delivery if the signal is detected.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF VARIOUS EMBODIMENTS

Figure 1:
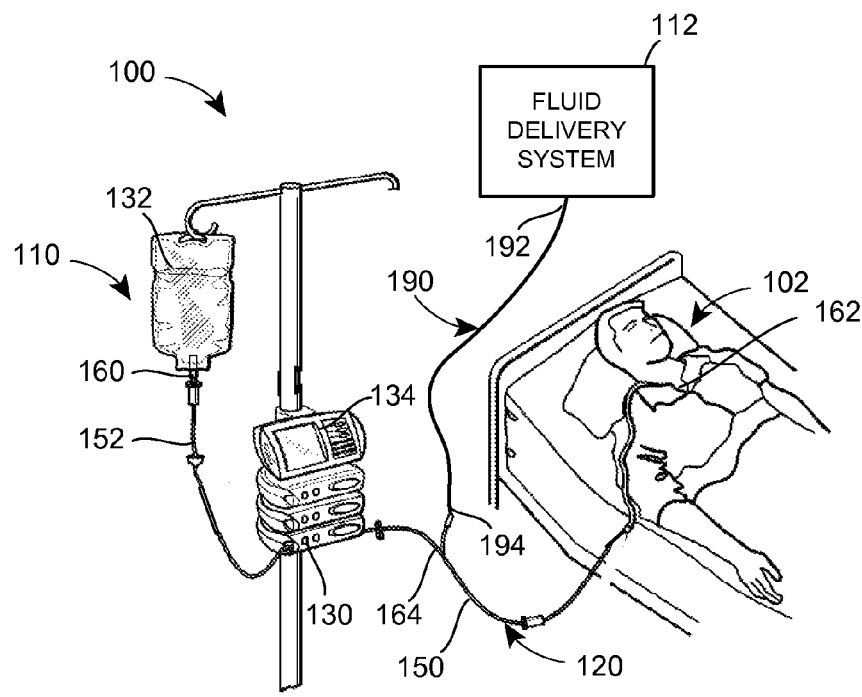
FIG. 1 is a schematic view of a healthcare delivery system and a system for alerting a user to a potential unintended bolus delivery according to the present disclosure.

According to the present disclosure, a method of alerting a user to a potential for an unintended bolus delivery is provided. According to this method, a signal is preferably transmitted prior to a change in the delivery of a fluid to the patient along a fluid flow path, or, alternatively, is transmitted shortly thereafter where, for example, the potential for adverse reaction to an unintended bolus is not significant. If this signal is detected, for example, by a delivery system already providing fluid to the patient, an alarm may be actuated to alert the user to the potential for an unintended bolus delivery. In addition, the change in the delivery of the fluid to the patient may be interrupted until such time as the interrupt is overridden, which may provide the user an opportunity, according to certain embodiments, to check for a connection that could lead to an unintended bolus condition, and in other embodiments, to check the effect of administering a bolus to the patient as a consequence of the delivery of the fluid.

This method may be carried out by a system for alerting a user to a potential unintended bolus delivery that includes a first fluid delivery system, a second fluid delivery system and a controller, which controller may be part of the first or second fluid delivery systems. The first delivery system may be in fluid communication with a patient along a first fluid flow path, and may include a receiver in communication with the first fluid flow path. The second delivery system may be in fluid communication with the patient along a second fluid flow path connected to the first fluid flow path between the first delivery system and the patient. The second delivery system may include a transmitter in communication with the second fluid flow path and configured to provide a signal prior to initiation of the second fluid delivery system to change fluid delivery to the patient, or shortly thereafter. Moreover, the controller may be coupled to the receiver, and may be programmed to determine if the signal has been received by the receiver and to alert the user to a potential unintended bolus delivery if the signal has been received by the receiver. The controller may also interrupt the initiation of the second fluid delivery system until overridden by the user.

Alternatively, the first delivery system may include a transmitter in communication with the first fluid flow path, and the second delivery system may include a receiver in communication with second flow path. The controller may be coupled to the receiver, and may be programmed to determine if a signal has been received by the receiver from the transmitter of the first delivery system, and to alert the user to a potential unintended bolus delivery if the signal has been received by the receiver.

As a further alternative, such a method may be carried out by a system without a communication link formed by the first and second fluid flow paths. For example, the second delivery system may provide a signal prior to the change in the delivery of fluid along the second flow path, which second fluid flow path may or may not be connected to the first fluid flow path. According to such an embodiment, the first delivery system may detect the signal from the second delivery system, and may actuate an alarm or otherwise alert the user to the potential to an unintended bolus condition. This alert may be provided by the first delivery system, or the first delivery system may provide a response over the communication link, and the second delivery system may alert the user to the potential for an unintended bolus condition.

The method and system according to this disclosure may now be discussed in detail with reference to FIGS. 1-8.

Figure 2:
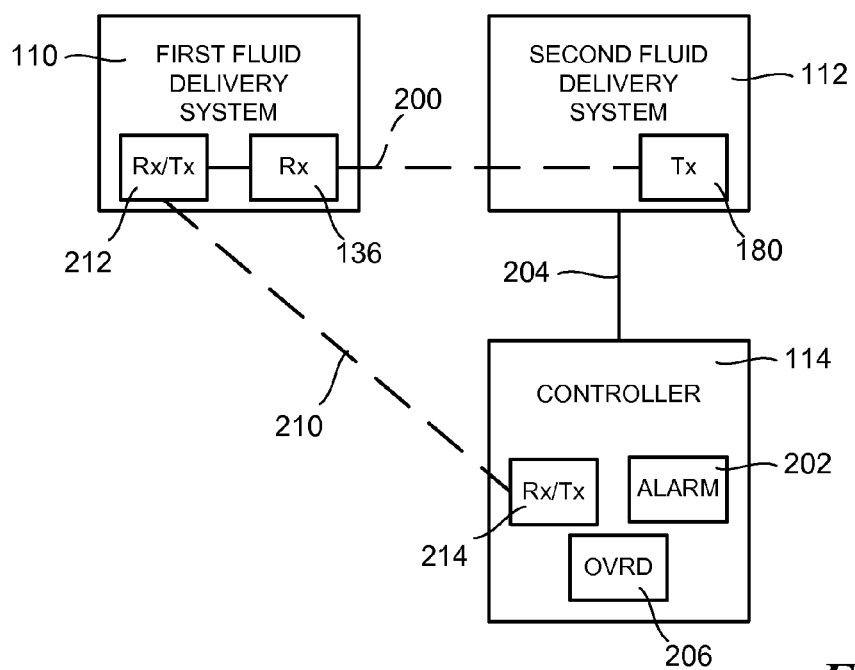
FIG. 2 is an enlarged schematic view of an embodiment of the system for alerting the user of FIG. 1 illustrating the communication links between the various components of the system incorporating a communication link along the flow path.
Figure 3:
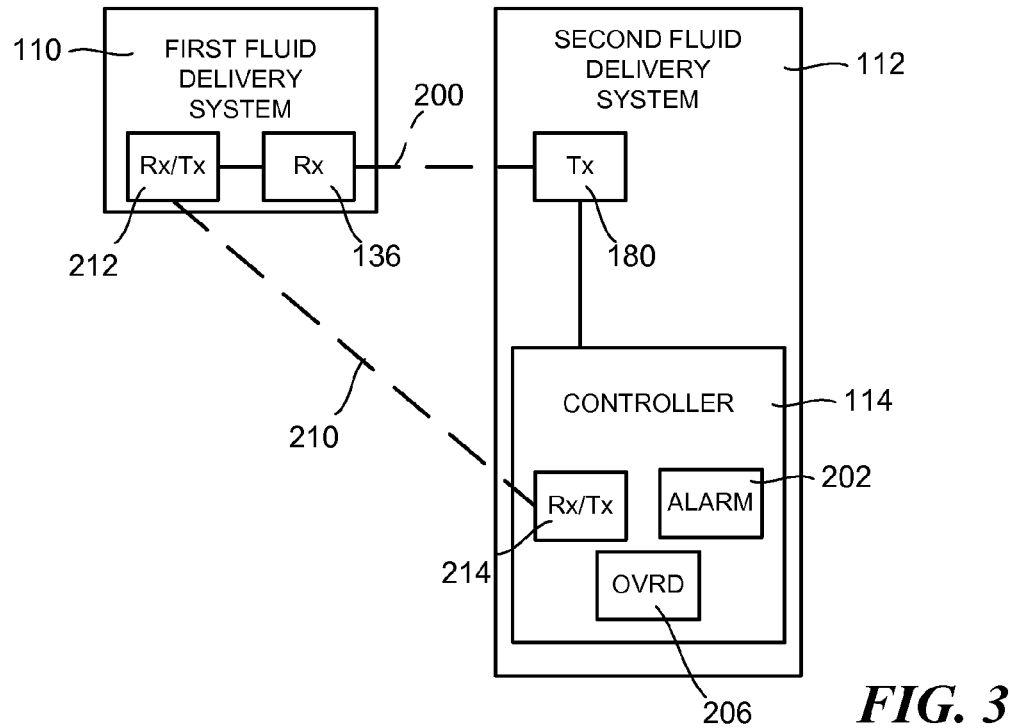
FIG. 3 is an enlarged schematic view of another embodiment of the system for alerting the user of FIG. 1 illustrating the communication links between the various components of the system incorporating a communication link along the flow path.
Figure 4:
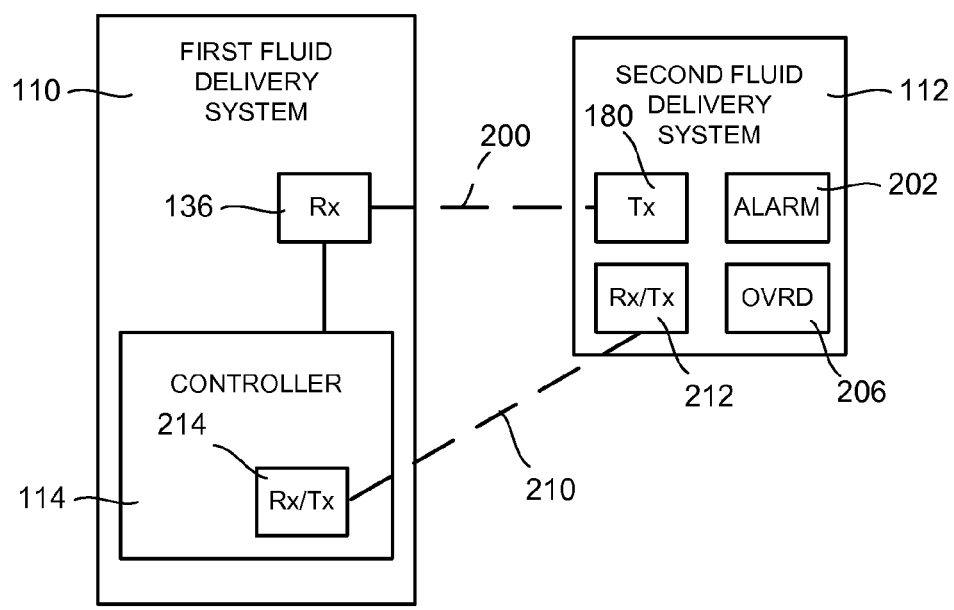
FIG. 4 is an enlarged schematic view of a further embodiment of the system for alerting the user of FIG. 1 illustrating the communication links between the various components of the system incorporating a communication link along the flow path.
Figure 5:
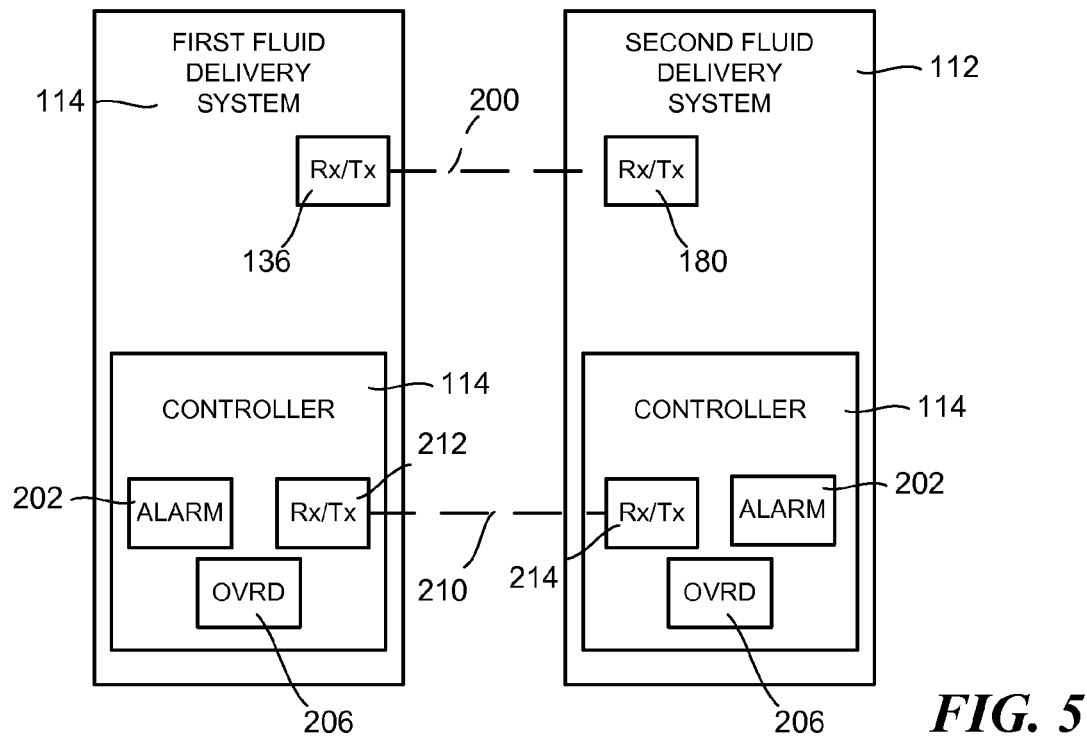
FIG. 5 is an enlarged schematic view of a still further embodiment of the system for alerting the user of FIG. 1 illustrating the communication links between the various components of the system incorporating a communication link along the flow path.

As illustrated in FIG. 1, a system 100 for alerting a user to a potential unintended bolus delivery to a patient 102 is provided. The system 100 may include a first fluid delivery system 110, configured to deliver a first medication to the patient 102, and a second fluid delivery system 112 configured to deliver a second medication to the patient 102. As illustrated in FIGS. 2-5, the system 100 may also include a controller 114, which may be a feature of the system 100 separate and apart from the first and second fluid delivery systems 110, 112 as illustrated in FIG. 2 or may be included within the first fluid delivery system 110 and/or the second fluid delivery system 112 as illustrated in FIGS. 3-5.

Returning to FIG. 1 and to the first fluid delivery system 110, it will be recognized that the delivery system 110 may be in fluid communication with the patient 102 along a first fluid flow path 120, and as noted previously may deliver a first fluid to the patient, which fluid may include a first medication or drug. To this end, the first delivery system 110 may include a first pump 130 and at least one first fluid container 132. As illustrated, the first pump 130 may be a peristaltic pump, and the first fluid container 132 may be a flexible-walled bag. The first fluid delivery system 110 may include other equipment as well, including a pump controller 134 and a receiver 136 (see, e.g., FIG. 2), the details of which will be discussed in greater detail below.

The first fluid flow path 120 comprises at least one set 150, 152 connected at a first end 160 of the first fluid flow path 120 to the first fluid container 132 and at a second end 162 of the first fluid flow path 120 to the patient 102. The set or sets may include a connector or connection 164 disposed between the first and second ends 160, 162; as illustrated, this connection 164 may be a Y-site connection. It will be appreciated that this connection 164 may be one of many connectors or connection sites disposed along the fluid flow path 120. It will also be recognized that the fluid flow path 120 may include other devices or equipment as well, such as spikes, drip chambers, clamps, etc.

While not illustrated in the same detail in FIG. 1, the second fluid delivery system 112 may include much the same equipment as the first fluid delivery system 110, such as the pump and the container, which pump may be a peristaltic pump and which container may be a flexible-walled bag. Further, the second fluid delivery system 112 may include a pump controller and a transmitter 180, as illustrated in FIG. 2. This fluid delivery system 112 may be in fluid communication with the patient 102 along a second fluid flow path 190 connected to the first fluid flow path 120 between the first fluid delivery system 110 and the patient 102. This second fluid flow path 190 may include at least one set connected at a first end 192 of the second fluid flow path 190 to a fluid container and at a second end 194 of the second fluid flow path 190 to a connector or connection, in particular at the Y-site connection 164 as illustrated.

According to certain embodiments of the present disclosure, the first fluid delivery system 110 is configured to deliver fluid to the patient at a first fluid flow rate, and the second fluid delivery system 112 is configured to deliver fluid to the patient at a second fluid flow rate that increases a combined delivery rate by a clinically relevant amount. In certain embodiments, the second flow rate may be greater than the first fluid flow rate. In some embodiments, the second fluid flow rate may be a multiple of the first fluid flow rate. In other embodiments, the second fluid flow rate may be at least an order of magnitude greater than the first fluid flow rate.

For example, consider an embodiment wherein the first fluid delivery system 110 provides a first fluid flow rate of 10 ml/hr, and the second fluid delivery system 112 provides a second fluid flow rate of 300 ml/hr. The second fluid flow rate is thus 30 times greater than the first fluid flow rate. The second fluid flow rate is also at least one order of magnitude (10×) larger than the first fluid flow rate.

Under these conditions, initiation of the second fluid delivery system 112 may cause the administration of a bolus to the patient by forcing the fluid already being delivered along the first fluid flow path 120 between the connection 164 and the patient 102 into the patient 102 over a very short period of time. Assuming an inner diameter of 2.5 mm for the line between the connection 164 and the patient 102 and a length of approximately 1 m, approximately 4.9 ml of the fluid being delivered by the first fluid delivery system is disposed along the first fluid flow path 120 between the connection 164 and the patient 102. If the second fluid delivery system 112 is activated while the first fluid delivery system 110 remains active, it is believed that the rate of fluid flow along the first fluid flow path 120 downstream of the connection 164 increases from 10 ml/hr to 310 ml/hr. As such, the 4.9 ml of the fluid from the first fluid delivery system 110 would be administered to the patient in approximately 57 seconds, instead of the nearly 30 minutes it would have taken using the fluid flow rate provided by the first delivery system 110 alone.

It will be further recognized that delivery of any medication over a compressed timeframe may have undesirable, even life-threatening, effects on the patient. Consequently, the system 100 incorporates equipment to provide an alert to the user of the second fluid delivery system 112 to the potential for this bolus to be administered to the patient, which equipment may, at least in part, already be part of the delivery systems 110, 112 but in other embodiments may be added after manufacture, as a kit for example. Under certain conditions, the bolus may be acceptable, or even desirable. However, at a minimum, the present system 100 alerts the user the potential for this bolus administration; according to certain embodiments, the delivery of the fluid from the second fluid delivery system is interrupted or prevented to prevent the administration of the bolus until a user can make a determination if the bolus is acceptable or desirable.

Moreover, it will also be recognized that while an example has been provided where the initiation of the second delivery system 112 involves providing a fluid along the second fluid flow path 190 in a setting where no fluid was previously delivered along the second fluid flow path 190, the present disclosure is not so limited. Instead, the change in delivery of the fluid to the patient may include situations wherein the second delivery system 112 has been delivering fluid to the patient along the second fluid flow path 190 at a first non-zero rate, and the change involves an increase in the delivery of fluid to the patient to second rate, such as may occur when initiating a modification or titration to an existing infusion. The change in delivery of fluid to the patient would thus encompass both starting an infusion where no infusion had previously been provided (changing from zero to a non-zero delivery rate) and adjusting an infusion to from a first delivery rate to a second delivery rate.

Therefore, as mentioned previously, the first fluid delivery system 110 has a receiver 136 in communication with the first fluid flow path 120, and the second fluid delivery system 112 has a transmitter 180 in communication with the second fluid flow path 190. Moreover, the second fluid delivery system 112, and in particular the transmitter 180, may be configured to provide a signal prior to initiation of the second fluid delivery system 112 to change fluid delivery to the patient 102 (or shortly thereafter). The signal transmitted by the transmitter 180 may travel along the length of the second fluid flow path 190 and the connected fluid flow path 120 (which may define a communication link 200, as illustrated in FIG. 2), and be received or detected by the receiver 136, whereupon further actions may be taken to alert the user and, optionally, interrupt operation of the second fluid delivery system 112. The signal may be coded to identify the second delivery system 112 relative to other delivery systems that might be in use at the same time.

According to certain embodiments of the present disclosure, the transmitter 180 may be an acoustical transmitter, and thus the receiver 136 may be an acoustical receiver. Alternatively, the transmitter 180 may be an RF transmitter, and the receiver 136 may be an RF receiver. Other alternative embodiments for the transmitter 180 and the receiver 136 will be recognized as well, which embodiments may use the flow paths 120, 190 to pass the signal between transmitter and receiver. It will also be recognized that the transmitter 180 may be defined by a first transceiver (transmitter and receiver), and the receiver 136 is defined by a second transceiver, which embodiment may permit two-way communication between the first and second fluid delivery systems 110, 112 along the communication link 200. As a still further alternative, the first fluid delivery system 110 may include a transmitter, and the second fluid delivery system 112 may include a receiver.

As mentioned previously, the system 100 also includes a controller 114, best seen in FIG. 2. This controller 114 may be coupled to the receiver 136, and may be programmed to determine if the signal has been received by the receiver 136 and to alert the user to a potential unintended bolus delivery if the signal has been received by the receiver 136, for example by actuating an alarm 202. Such a controller 114 alternatively may be programmed to determine if a signal is received by the receiver if the receiver is instead included in the second fluid delivery system 112, and the transmitter is included in the first fluid delivery system 110. In fact, the controller 114 may also be programmed to interrupt initiation of the second fluid delivery system 112 prior to (or shortly after) a change in delivery of fluid to the patient 102 by the second fluid delivery system 112. To this end, the controller 114 may be coupled to the second fluid delivery system 112 (e.g., to the associated pump) via a connection 204. Moreover, the controller may include an override input (e.g., button) 206 to permit the user to override the interruption of the initiation of the second fluid delivery system 112.

As to the coupling between the controller 114 and the receiver 136, this may take a variety of forms. According to the embodiment illustrated in FIG. 2, the controller 114 is coupled via a communication link 210 to the receiver 136. According to this embodiment, the first fluid delivery system 110 may include an RF transmitter 212 coupled to the receiver 136, and the controller 114 may include an RF receiver 214, the communication link 210 being an RF link between the RF transmitter 212 and the RF receiver 214. It will be recognized that other communication links may be used instead, such as infrared links or hardwired/cable connections, and that the RF transmitter 212 and receiver 214 may be defined by transceivers, as illustrated.

According to certain embodiments, the link 210 may be used not only to confirm detection of the signal at the receiver 136, but to transmit information from the first delivery system 110 to the controller 114/second delivery system 112. For example, the first delivery system 110 may transmit and the controller 114/second delivery system 112 may receive information over the communication link 210 regarding the first medication delivered to the patient 102 by the first fluid delivery system 110. This information may be displayed to the user of the system 110 (e.g., the nurse or other healthcare professional) at the same time the controller 114 actuates the alarm 202. Other information, such as the delivery rate of the first medication, may also be communicated over the communication link 210.

As noted above, the controller 114 may be coupled to an alarm 202, and the controller 114 may be programmed to actuate the alarm 202 if the signal has been received by the receiver 136. Of course, where the controller 114 is part of or integrated into the second fluid delivery system 112, it may also be possible to refer to the second delivery system 112 as coupled to or including the alarm 202. In any event, the alarm 202 may include any number of devices, such as an audible alarm, a visual alarm or combinations thereof. In fact, the alarm 202 may be defined by equipment provided to perform that function for the second delivery system 112 for other reasons, or the alarm 202 may be defined by equipment dedicated to providing the user with an alert as to the potential unintended bolus.

Figure 6:
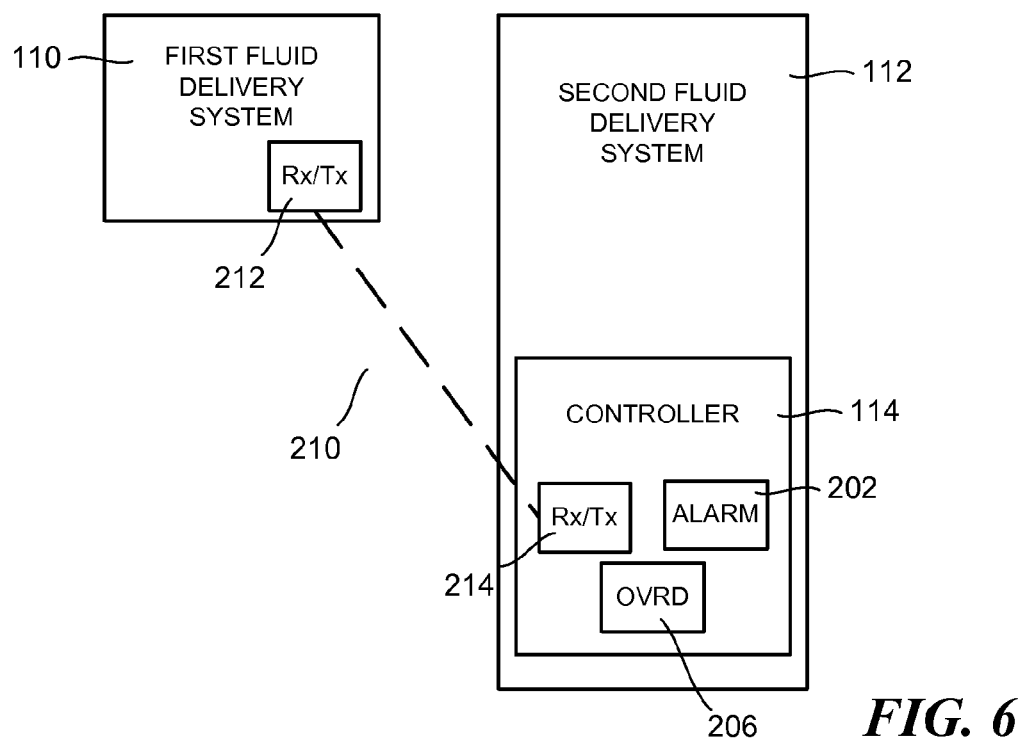
FIG. 6 is an enlarged schematic view of an additional embodiment of the system for alerting the user of FIG. 1 illustrating the communication links between the various components of the system without a communication link along the flow path.
Figure 7:
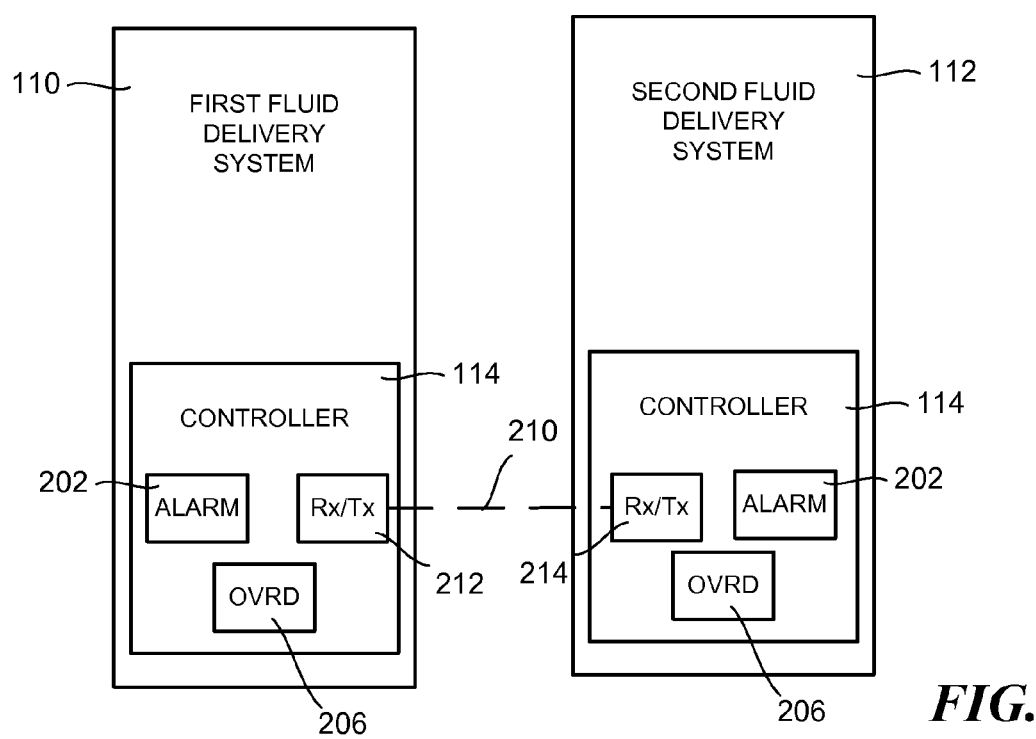
FIG. 7 is an enlarged schematic view of an embodiment of the system for alerting the user of FIG. 1 illustrating the communication links between the various components of the system without a communication link along the flow path.
Figure 8:
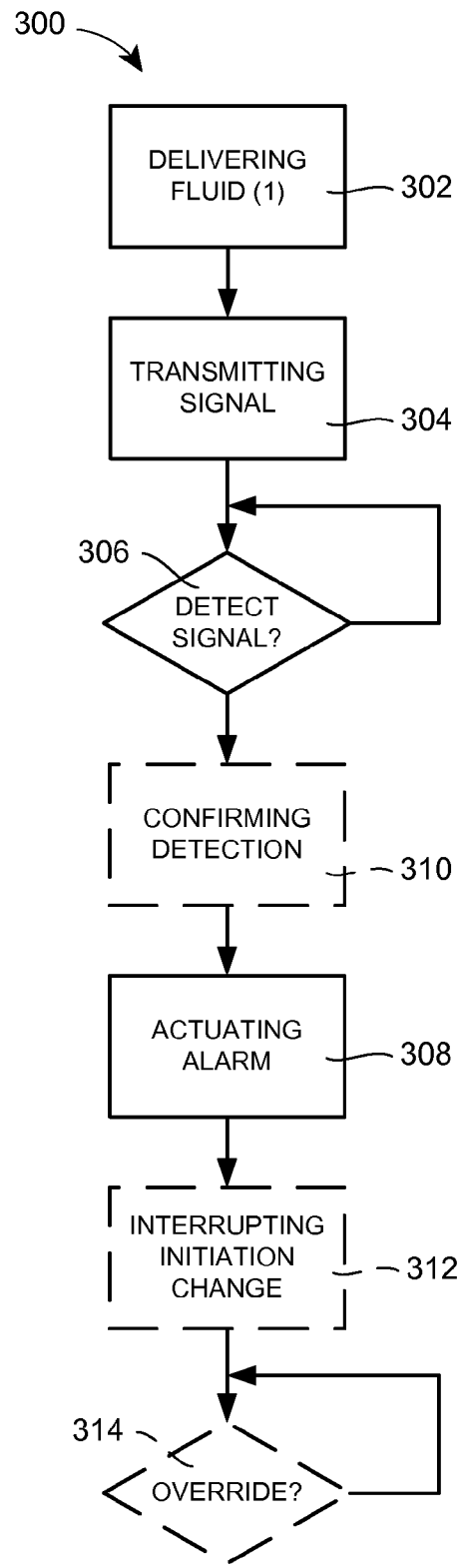
FIG. 8 is a flowchart of a method of alerting a user to a potential unintended bolus delivery as may be performed by a system such as is illustrated in FIGS. 1-7.

As alluded to above, the system 100 is not limited to the specific arrangement discussed in FIGS. 1 and 2. For example, several different embodiments of the system 100 are illustrated in FIGS. 3-5 and 6-7. The general characteristic differentiating those illustrated in FIGS. 3-5 from those illustrated in FIGS. 6-7 is the presence or absence of a communication link along the flow paths 120, 190, those illustrated in FIGS. 3-5 being similar to that illustrated in FIG. 2 in that they include a communication link along the flow paths 120, 190.

FIG. 3 illustrates an embodiment of the system 100 wherein the controller 114 is incorporated into the second delivery system 112. This embodiment shares many characteristics with the embodiment of FIG. 2, in that the there is a first communication link 200 formed between a receiver 136 that is an element of the first delivery system 110 and a transmitter 180 that is an element of the second delivery system 112, and a second communication link 210 formed between a transceiver 212 associated with the first fluid delivery system 110 and a transceiver 214 associated with the controller 114, which controller is now part of the second fluid delivery system 112, and thus may be discussed as a transceiver 214 associated with the second delivery system 112 as well. One principal difference between the embodiment illustrated in FIG. 2 and that of FIG. 3 is that the coupling between the second delivery system 112 and the controller is an internal one, instead of an external one.

As illustrated in FIG. 4, the system 100 includes a controller 114 incorporated into the first delivery system 110. As a consequence of the incorporation of the controller 114 into the first delivery system 110, the communication link 210 formed between the transceivers 212, 214 is used to connect the first and second delivery systems 110, 112, instead of the first delivery system 110 to the controller 114. The receiver 136 is coupled to the controller 114 by an internal connection, and the communication link 210 is established between the transceivers 212, 214 to communicate the confirmation of the receipt of the signal at the receiver 136, and to communicate the interrupt signal to the second fluid delivery system 112. According to this embodiment, the alarm 202 and the override input 206 are integrated as part of the second fluid delivery system 112, so that the alert is provided at the point in the system 100 where the action principally causing the bolus condition to take place is occurring, and thus the actuation of the alarm 202 causes the user's attention to be focused on this element. Similarly, the placement of the override input 206 at this point again focuses the user's attention on this aspect of the overall system 100.

One further embodiment is illustrated in FIG. 5, wherein separate controllers 114 are incorporated into both the first delivery system 110 and the second delivery system 112. As such, the receiver 126 and the transmitter 180 are defined by transceivers, because according to this embodiment, it is equally possible for a particular delivery system 110, 112 to be designated the first delivery system or the second delivery system. In this regard, each system 110, 112 also includes the alarm 202 and the override input 206, so as to permit this equipment to be associated with whichever delivery system is designated, by virtue of the order of initiation of operation, as the second delivery system 112.

The embodiment illustrated in FIG. 5 may have certain advantages over those illustrated in FIGS. 2-4, in that every delivery system may be designated as the first delivery system or the second delivery system. Additionally, such an embodiment would permit the first delivery system 110 to transmit a signal that is received by the second delivery system 112, which signal is used by the controller 114 to interrupt delivery from the second delivery system 112 prior to or shortly after delivery by the second delivery system 112. It does, however, require additional hardware than the embodiments illustrated in FIGS. 2-4, in that it requires the receiver 136 and the transmitter 180 to be defined by a transceiver because a particular delivery system may fulfill either the role as the first or second delivery device. Additionally, each delivery system 110, 112 includes the alarm 202 and override input 206. It will be recognized that where the role of the controller 114 is performed by a pump controller, such as the pump controller 134 illustrated in FIG. 1, that is already part of the first or second delivery system 110, 112, the alarm 202 may be defined by existing equipment of the system 110, 112 that fulfills other roles for the system 110, 112.

It is also possible to define an embodiment of the system 100 wherein the communication link 200 does not exist. Instead, while a signal is transmitted by the second delivery system 112 prior to (or shortly after) initiation of the change of fluid delivery by the second delivery system 112 to the patient 102, it does not pass along the flow paths 120, 190. Rather, the communication link 210 is used for all communications between the first delivery system 110 and the second delivery system 112.

Moreover, because the flow paths 120, 190 are not used to pass the signal between the first and second delivery systems, the system 100 according to these embodiments may transmit the signal from the second delivery system 112 to the first delivery system 110 even when the second fluid flow path is not connected to the first fluid flow path. That is, when the first and second flow paths 120, 190 are used to pass the signal from the second delivery system 112 to the first delivery system 110, if the connection is not made between the flow paths 120, 190, then no further action is taken, which is acceptable because there is physical confirmation that the flow paths 120, 190 are not connected (i.e., the signal does not travel from the transmitter 180 to the receiver 136), and thus the potential for an unintended bolus, as explained herein, is not present. However, when the first and second flow paths 120, 190 are not used to carry the signal from the second delivery system 112 to the first delivery system 110, this physical confirmation of the connection of the paths 120, 190, and thus the potential for the unintended bolus, is not present. While other mechanisms and methods may be used to make the first and second delivery systems 110, 112 aware of the connection (e.g., 166) and thus the potential for an unintended bolus, a simpler solution may be for the second delivery system 112 to determine if there are any other operable systems (e.g., the first delivery system 110) in the immediate area, and then alert the user of the second delivery system 112 of the potential for an unintended bolus administration, and the need to make a physical inspection of the connections and, potentially, the consequences of such an unintended bolus.

FIGS. 6 and 7 illustrate two embodiments that do not use the link 200, but instead rely upon the communication link 210 for carrying out a method according to the present disclosure.

In particular, FIG. 6 illustrates an embodiment wherein the controller 114 and the associated alarm 202 and, optionally, the override button 206 are incorporated into the second delivery system 112. Prior to initiation of change in fluid delivery from the second fluid delivery system 112, a signal is sent from the transceiver 214 to the transceiver 212. In response, the first delivery system 110 may provide a signal back to the second fluid delivery system 112, informing the second delivery system 112 of the preexisting fluid administration occurring along the fluid path 120, and information such as the medication being delivered. The first fluid delivery system 110 may also provide a confirmation of the receipt of the signal from the second delivery system 112 along the communication link 210, prior to sending the information regarding the preexisting administration and the identification of the medication being administered. In response to all or part of the information received from the first delivery system 110, the controller 114 may alert the user to the need to inspect the flow path from the second delivery system 112 to the patient 102 for the connection (e.g., Y-site connection 164) that might give rise to an unintended bolus condition, and optionally to interrupt the change in administration of the fluid along the second fluid flow path 190 until such time as the user uses the override input 206 to begin the infusion using the second delivery system.

It will be recognized that the embodiment of FIG. 6 may also be configured to permit the second fluid delivery system 112 to receive a signal from the first fluid delivery system 110, in keeping with the alternative embodiments discussed above, the receipt of the signal resulting in an alarm, and optionally interruption of the change in administration.

FIG. 7 differs from FIG. 6 in a fashion similar to the manner in which FIG. 5 differs from the embodiments illustrated in FIGS. 2-4. FIG. 7 illustrates a system 100 where the first and second delivery systems 110, 112 are defined by delivery systems having similar hardware, with a controller 114 incorporated into both the delivery system 110 and the delivery system 112 and that controller 114 having an alarm 202 and override input 206 associated therewith. However, as to the overall operation of the system 100 illustrated in FIG. 7, it is similar to the operation of the system 100 illustrated in FIG. 6, in that the communication occurs along the communication link 210 separate and apart from the fluid flow paths 120, 190.

It will also be recognized that the communication link could in fact be internal to the controller 114. That is, in a still further embodiment of the present disclosure, the controller 114 is common to both the first and second delivery systems 110, 112. Consequently, rather than requiring an external communication link or links, the signal provided prior to the initiation of delivery using the second fluid delivery system 112 may be internal to the controller 114, as may the detection of the signal, and the actuation of the alarm. Of course, according to certain embodiments, this common controller may not know if the connection between the fluid flow paths 120, 190 exists, while according to other embodiments, the signal may be sent along the fluid flow paths 120, 190 with the receiver 136 and the transmitter 180 coupled directly to the common controller 114, rather than through other aspects of the fluid delivery systems 110, 112.

Having thus described several embodiments of a system 100 according to the present disclosure, a method 300 that may be performed using the system 100 or other such systems may now be discussed with reference to FIG. 3.

A method 300 of alerting a user to a potential unintended bolus delivery begins at block 302 with delivery of the fluid to the patient 102 along the first fluid flow path 120. The method 300 also includes transmitting a signal at block 304 prior to a change in delivery of a fluid to the patient along the second fluid flow path 190, which may be connected to the first fluid flow path 120. As seen with reference to the embodiments of the system 100 illustrated in FIGS. 2-5 and 6-7, this signal (which may be an acoustical or an RF signal, for example) may be sent over the link 200 defined along a second fluid flow path 190 connected to the first fluid flow path 120 upstream of the patient 102, or over the link 210 defined between transceivers 212, 214. This signal is detected at block 306, which detection may occur over the link 200 defined along the first fluid flow paths 120, 190 or the link 210. In addition, the method 300 includes, at block 308, actuating an alarm, such as the alarm 202, to alert the user to a potential unintended bolus delivery if the signal is detected.

It will be recognized that the actions represented in each of the blocks 302, 304, 306, 308 may be described in greater detail, for example with reference to the system 100. Accordingly, delivering the fluid to the patient 102 along the fluid flow path 120 may include actuating the first delivery system 110. Also, transmitting a signal may include, with reference to the embodiments of FIGS. 2-5, actuating the transmitter 180 associated with the second delivery system 112 prior to (or shortly after) initiation of the second delivery system 112 to change fluid delivery to the patient 102. Further, the action of detecting the signal may include the action of receiving the signal at the receiver 136. Likewise, the action of actuating the alarm (which may be an audible or a visual alarm, for example) if the signal is detected may include not only the actuation of the alarm 202 by the controller 114, but may also include the communication of the detection of the signal over the communication link 210 between the transceiver 212 (coupled to the receiver 136 and associated with the first fluid delivery system 110) and the transceiver 214 (associated with the controller 114) (see block 310).

Indeed, the same communication link 210 used to report the detection of the signal may be used to report information regarding a medication in the fluid delivered to the patient along the first fluid flow path 120.

It is also true that the method 300 may include other actions beyond those represented in blocks 302, 304, 306, 308, and 310. For example, the method 300 may include interrupting a change in delivery of a fluid to the patient 102 along the second fluid flow path 190 at block 312, for example by the controller 114 sending an interrupt signal along link 204 to the second delivery system 112. The method 300 may also include, at block 314, permitting the user to override the interruption of the delivery of a fluid to the patient along the second fluid flow path, which may be carried out through the actuation of the override input 206.

Moreover, it will be recognized that the step of delivering fluid to the patient along the first fluid flow path 120 may include delivery at a first fluid flow rate, and the step of transmitting a signal comprises transmitting a signal along a second fluid flow path 190 prior to a change in delivery of a fluid to the patient along the second fluid flow path 190 at a second fluid flow rate that increases the overall delivery rate by a clinically relevant amount. In certain embodiments, the second flow rate may be greater than the first fluid flow rate, similar to particular embodiments discussed above. Similarly, the second fluid flow rate may be a multiple of the first fluid flow rate, or even at least an order of magnitude greater than the first fluid flow rate, according to other embodiments discussed above.

The system 100 and the method 300 may provide advantages as detailed above, and other additional advantages as well. In particular, the system 100 and the method 300 permit a single IV injection site to be used for the administration of multiple fluids with a reduced risk of an unintended bolus condition. As a consequence, the system 100 and method 300 preserves the advantages of a single IV injection site (e.g., reduced trauma to the patient and risk of inadvertent separation), while minimizing this risk through warnings to the user and, optionally, interruption of delivery of at least one of the fluids to the patient. Moreover, this may be achieved in certain embodiments with a minimal amount of additional hardware included in the system 100.

Although the foregoing text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

For example, while only two fluid delivery systems are illustrated to simplify the disclosure, it will be recognized that the system for alerting a user to a potential unintended bolus delivery may include or involve a greater number of delivery systems in fluid communication with the patient and in communication with each other. Similarly, certain numbers of controllers and pump controllers have been illustrated in the various embodiments, the numbers used in other embodiments of the system may exceed those illustrated.

Moreover, it will be understood that the controllers and pump controllers disclosed herein may include a processor, a memory, one or more network interfaces, one or more input/output interfaces, and other well known components; to this extent, the controllers may be referred to as "computer" or "computerized" controllers. The controllers may execute programs to carry out the methods disclosed herein; to this extent, the controllers may be referred to as "programmed" or "programmable" controllers, while not suggesting that they are necessarily programmable logic controllers. As used herein, the term "program" or "programmed" refers to computer program logic used to provide the specified functionality. Thus, a program can be implemented in hardware, firmware, and/or software. Programs may be stored on or in a storage device, loaded into memory, and executed by a processor, or may be provided from program products that are stored in tangible computer-readable storage mediums (e.g. RAM, hard disk, or optical/magnetic media). In addition, the memory referred to above may be in the form of random access memory (RAM) and read-only memory (ROM), and the ROM may take many different forms, including erasable programmable ROM (EPROM) and electrically erasable programmable ROM (EEPROM).

It should also be understood that, unless a term is expressly defined in this patent using the sentence "As used herein, the term '_____' is hereby defined to mean . . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:

1. A system for alerting a user to a potential unintended bolus delivery, the system comprising:
a first fluid delivery system comprising a first fluid flow path, the first fluid delivery system configured to be in fluid communication with a patient along the first fluid flow path,
the first fluid delivery system having a receiver;
a second fluid delivery system comprising a second fluid flow path, the second fluid delivery system configured to be in fluid communication with the patient along the second fluid flow path, the second fluid flow path connected to the first fluid flow path between the first fluid delivery system and the patient, the second fluid delivery system having a transmitter in communication with the receiver and configured to provide a signal that travels along the second fluid flow path prior to initiation of the second fluid delivery system to change fluid delivery to the patient from the second fluid delivery system;

the receiver configured to detect the signal as it travels along the first fluid flow path; and a controller coupled to the receiver, the controller programmed to determine if the signal has been received by the receiver and to alert the user to a potential unintended bolus delivery if the signal has been received by the receiver.

2. The system according to claim 1, wherein:

the receiver is in communication with the first fluid flow path; and the transmitter is in communication with the second fluid flow path.

3. The system according to claim 1, wherein the controller is programmed to interrupt initiation of the second fluid delivery system prior to the change in fluid delivery to the patient from the second fluid delivery system.

4. The system according to claim 3, wherein the controller is programmed to permit the user to override the interruption of the initiation of the second fluid delivery system.

5. The system according to claim 4, wherein the controller is coupled via a communication link to the receiver.

6. The system according to claim 5, wherein the first fluid delivery system comprises an RF transmitter and the second fluid delivery system comprises an RF receiver, the communication link comprises the RF transmitter and the RF receiver, and the second fluid delivery system comprises the controller.

7. The system according to claim 6, where the controller receives information on the communication link regarding a medication delivered with the fluid to the patient by the first fluid delivery system.

8. The system according to claim 1, wherein the second fluid delivery system comprises an alarm actuated to alert the user to a potential unintended bolus delivery.

9. The system according to claim 1, wherein the first fluid delivery system is configured to deliver fluid to the patient at a first fluid flow rate and the second fluid delivery system is configured to deliver fluid to the patient at a second fluid flow rate that increases a combined delivery rate.

10. The system according to claim 9, wherein the second fluid flow rate is a multiple of the first fluid flow rate.

11. The system according to claim 10, wherein the second fluid flow rate is at least an order of magnitude greater than the first fluid flow rate.

12. The system according to claim 1, wherein the first fluid delivery system is configured to deliver a first medication to the patient, and the second fluid delivery system is configured to deliver a second medication to the patient.

13. The system according to claim 1, wherein the first fluid delivery system comprises a first pump and a first fluid container, and the second fluid delivery system comprises a second pump and a second fluid container.

14. The system according to claim 13, wherein the first and second containers comprise flexible-walled bags.

15. The system according to claim 14, wherein the first and second pumps each comprise a peristaltic pump.

16. The system according to claim 15, wherein:

the first fluid flow path comprises at least one set connected at a first end of the first fluid flow path to the first fluid container and configured to be connected at a second end of the first fluid flow path to the patient, the at least one set comprising a connector disposed between the first and second ends, and the second fluid flow path comprises at least one set connected at a first end of the second fluid flow path to the second fluid container and at a second end of the second fluid flow path to the connector.

17. The system according to claim 16, wherein the connector comprises a Y-site connection.

18. The system according to claim 1, wherein the controller is coupled to an alarm, the controller programmed to actuate the alarm if the signal has been received by the receiver.

19. The system according to claim 18, wherein the alarm comprises an audible alarm or a visual alarm.

20. The system according to claim 1, wherein the transmitter is an acoustical transmitter and the receiver is an acoustical receiver.

21. The system according to claim 1, wherein the transmitter is an RF transmitter and the receiver is an RF receiver.

22. The system according to claim 1, wherein the transmitter is defined by a first transceiver, and the receiver is defined by a second transceiver.

* * * * *